United States Patent
McEwen et al.

[11] Patent Number: 5,935,146
[45] Date of Patent: *Aug. 10, 1999

[54] METHOD FOR MONITORING THE PATENCY OF PNEUMATIC TUBING

[76] Inventors: James A. McEwen, 15510 Bamberton Drive, Richmond, B.C., Canada, V7A 1K6; Michael Jameson, 2365 Badger Road, North Vancover, B.C., Canada, V7G 1S9

[*] Notice: This patent is subject to a terminal disclaimer.

[21] Appl. No.: 08/959,262

[22] Filed: Oct. 28, 1997

Related U.S. Application Data

[63] Continuation of application No. 08/700,582, Aug. 12, 1996, Pat. No. 5,681,339.

[51] Int. Cl.[6] ........................................... A61B 17/00
[52] U.S. Cl. ........................ 606/202; 606/203; 128/898
[58] Field of Search .................................. 606/201–204; 128/898

[56] References Cited

U.S. PATENT DOCUMENTS

| | | |
|---|---|---|
| 3,892,229 | 7/1975 | Taylor et al. . |
| 4,013,069 | 3/1977 | Hasty . |
| 4,326,416 | 4/1982 | Fredberg . |
| 4,469,099 | 9/1984 | McEwen . |
| 4,479,494 | 10/1984 | McEwen . |
| 4,520,819 | 6/1985 | Birmingham et al. . |
| 5,681,339 | 10/1997 | McEwen ................................ 606/202 |

*Primary Examiner*—Glenn K. Dawson
*Attorney, Agent, or Firm*—ipsolon llp

[57] ABSTRACT

A method of monitoring the patency of an inflated tube in a pneumatic medical device. The method includes inflating the tubing of the device, generating a pneumatic pulse at one part of the tubing by varying pressure in the tubing, sensing at another part of the tubing the variation of the pressure, determining the time between the generated and sensed pressure, and producing a human-perceptible signal when the time between the generated and sensed pressure exceeds a reference level.

6 Claims, 5 Drawing Sheets

METHOD FOR MONITORING THE PATENCY OF PNEUMATIC TUBING

This a continuation of U.S. application Ser. No. 08/700,582, filed on Aug. 12, 1996, now U.S. Pat. No. 5,681,339.

FIELD OF THE INVENTION

This invention pertains to pneumatic medical devices such as pneumatic tourniquet systems commonly used to facilitate surgical procedures and pneumatic limb compression systems commonly used in the prevention of deep vein thrombosis in patients and in the treatment of lymphedema. In particular, this invention pertains to a pneumatic medical device having an inflatable cuff or appliance attached externally to a patient and having an instrument connected by tubing to the inflatable cuff or appliance for controlling the pressure in the cuff or appliance to continuously or intermittently apply a constant pressure or a desired pressure waveform to the portion of the body beneath the inflatable cuff or appliance.

BACKGROUND OF THE INVENTION

Many types of pneumatic medical devices have an inflatable part attached externally to a patient and an instrument part connected by tubing to the inflatable part for controlling the pressure in the inflatable part in order to continuously or intermittently apply a constant pressure or a desired pressure waveform to the portion of the body beneath the inflatable part. Two common type of devices are pneumatic tourniquet systems for surgery and limb compression systems for the prevention of deep vein thrombosis and treatment of lymphedema.

In a typical pneumatic tourniquet system, an inflatable cuff encircles a limb at a desired location and is connected pneumatically by flexible pneumatic tubing to a pressure controller which maintains the pressure in the cuff above a minimum pressure required to stop arterial blood flow in the limb distal to the cuff over a time period suitably long for the performance of a surgical procedure distal to the cuff location. Many types of such pneumatic tourniquet systems have been described in the prior art, such as those described by McEwen in U.S. Pat. Nos. 4,469,099, No. 4,479,494 and No. 5,439,477, and by McEwen and Jameson in U.S. Pat. App. 08/297,256 filed on Aug. 26, 1994.

In a typical limb compression system for the prevention of deep vein thrombosis and treatment of lymphedema, an inflatable appliance is attached to a limb and is connected by flexible pneumatic tubing to a pressure controller which controls the pneumatic pressure in the appliance to periodically inflate the appliance and thus periodically apply pressure to the underlying limb and augment the flow of venous blood proximally in the limb. Examples of such limb compression systems are given in U.S. Pat. No. 3,892,229 of Taylor et al. and in U.S. Pat. No. 4,013,069 of Hasty. Another example is given in pending U.S. Pat. App. 08/639,782 of McEwen and Jameson, filed on Apr. 29, 1996.

A common problem associated with the use of pneumatic tourniquet systems and limb compression systems relates to the flexible pneumatic tubing which establishes a pneumatic pathway between the pressure controller and the pneumatic cuff or appliance. The pressure controller is often located remotely from the patient, necessitating the use of long and very flexible tubing extending from the controller and around and between staff and other equipment to the patient. Pneumatic connectors are typically used to connect and disconnect the flexible tubing from the pressure controller, and from the cuff or appliance. During usage of tourniquet systems and limb compression systems, the patency of the tubing including the associated connectors, or the degree of pneumatic obstruction produced by the tubing, can change and seriously impair the function of such systems. For example, before or during use the tubing can become kinked and partially or completely obstructed, thus restricting pneumatic flow or completely isolating the pressure controller from the cuff or appliance, and thus preventing a desired pressure from being produced in the cuff or appliance. Also, through malfunction or operator error, the tubing can become disconnected from the pressure controller or from the cuff or appliance, again preventing a desired pressure from being produced in the cuff or appliance.

Birmingham et al. describe in U.S. Pat. No. 4,520,819 a tourniquet system with differential pressure occlusion detector for detecting certain types of tubing obstructions, but this invention is restricted to tourniquet systems which have two pneumatic tubes between the pressure controller and the pneumatic cuff, and the invention has other limitations.

The present invention incorporates an adaptation of the principles of acoustic reflectometry: by introducing a pneumatic pressure pulse of short duration into a pneumatic conduit and then analyzing reflections arising from the pressure pulse which occur when the pulse encounters a change in the cross sectional area of the conduit as it propagates throughout the conduit, by comparing the amplitude of the introduced pulse to the amplitude of the reflected pulse the pneumatic conduit may be characterized in terms of cross-sectional area and length. Such pneumatic conduits may be characterized in terms of cross-sectional area and length because any difference in the cross-sectional area at a particular location along the length of the conduit is proportional to the amplitude of the acoustic pulse reflected from the location, and the time delay until the reflected pulse is detected can be analyzed to determine the particular location along the length of the conduit. A more detailed explanation of the principle of acoustic reflectometry is included in U.S. Pat. No. 4,326,416 of Fredberg.

Techniques have been described in the prior art employing acoustic reflectometry to determine physical characteristics of passageways in living subjects, such as the airway, from measurements made at the mouth. See, for example, U.S. Pat. No. 4,326,416 and re-examination certificate B1 4,326,416 to Fredberg. Other techniques have been described in the prior art employing acoustic reflectometry and a wave tube in the nasal cavity of a subject to determine the shape of the nasopharyngeal cavity. See, for example, U.S. Pat. No. 5,316,002 to Jackson et al. In U.S. Pat. No. 5,445,144, Wodicka et al. described a technique employing acoustic reflectometry to guide the placement, determine position, and insure patency of a moveable tube or catheter within the body. The prior art does not describe techniques or apparatus for detecting or locating a partial obstruction, a complete obstruction, or a disconnection of tubing and associated connectors communicating pneumatically between a pressure controller and an inflatable cuff or sleeve of a pneumatic medical device attached externally to the body of a living subject at a fixed location and pressurized periodically or for an extended time period to achieve a therapeutic purpose.

SUMMARY OF THE INVENTION

The present invention provides apparatus and a method for monitoring the patency of tubing in pneumatic medical devices. More specifically, the present invention includes means for detecting and locating a partial obstruction, a complete obstruction, or a disconnection of tubing arid associated connectors communicating pneumatically between a pressure controller and a cuff or sleeve of a pneumatic medical device such as a pneumatic tourniquet system or a pneumatic limb compression system. In the present invention, changes in the cross-sectional area of the tubing communicating pneumatically between the pressure controller of a medical device and the cuff or appliance which are associated with partial or complete obstruction can be by detected and located by analyzing-changes in acoustic reflections which arise from those partial or complete obstructions. Similarly, changes in patency associated with disconnection of the cuff or appliance from the tubing, or associated with disconnection of the tubing from the pressure controller can be determined by analyzing changes in acoustic reflections from the pressure pulse.

The invention is directed to pneumatic medical apparatus comprising: an inflatable appliance for positioning onto the surface of a limb and adapted to apply pressure to the limb beneath the appliance when inflated with gas; tubing for establishing a pneumatic conduit between the inflatable appliance and a pressure control means; and pressure control means for supplying the tubing with gas at a controlled pressure, wherein the pressure control means includes pulse generating means for generating a pneumatic pulse at a sensing location in the tubing by producing a variation in the pressure of the gas at the sensing location during a finite time interval, and tubing patency monitoring means adapted to sense the variation of pneumatic pressure at the sensing location and produce a tubing obstruction signal when the variation of pneumatic pressure sensed after the finite time interval exceeds a reference level. The reference level may be a predetermined fraction of the maximum variation of pneumatic pressure sensed during the finite time interval.

Preferably, the tubing patency monitoring means of the present invention produces an elapsed time signal indicative of the elapsed time between the maximum variation of pneumatic pressure and the initiation of the tubing obstruction signal and estimates the position of the obstruction of the tubing corresponding to the elapsed time indicated by the elapsed time signal.

DESCRIPTION OF THE PREFERRED EMBODIMENT

The embodiment illustrated is not intended to be exhaustive or limit the invention to the precise form disclosed. It has been chosen and described in order to explain the principles of the invention and its application and practical use, and thereby enable others skilled in the art to utilize the invention.

The preferred embodiment as described is primarily directed towards monitoring the patency of pneumatic tubing comprising part of a medical device connecting an inflatable cuff or appliance to a pneumatic controller. The patency of the pneumatic tubing is monitored using the principals of acoustic reflectometry to detected and localize of obstructions occurring in the tubing. It will be apparent however, that the apparatus and methods herein described could also be applied to more fully determine the characteristics of a pneumatic system in terms of lengths and cross-sectional areas, and for example, be used to identify pneumatic accessories connected to a device.

To enable the reader to better understand the principles of the invention and appreciate the practical application of the invention it is described below incorporated into pneumatic tourniquet systems such as those described by McEwen in U.S. Pat. No. 4,469,099, No. 4,479,494 and No. 5,439,477, and by McEwen and Jameson in U.S. Pat. App. 08/297,256 filed on Aug. 26, 1994, all of which are herein incorporated by reference. The invention may also be incorporated into limb compression systems such as described in pending U.S. Pat. App. 08/639,782 of McEwen and Jameson, filed on Apr. 29, 1996, which is herein incorporated by reference.

Figure 1:
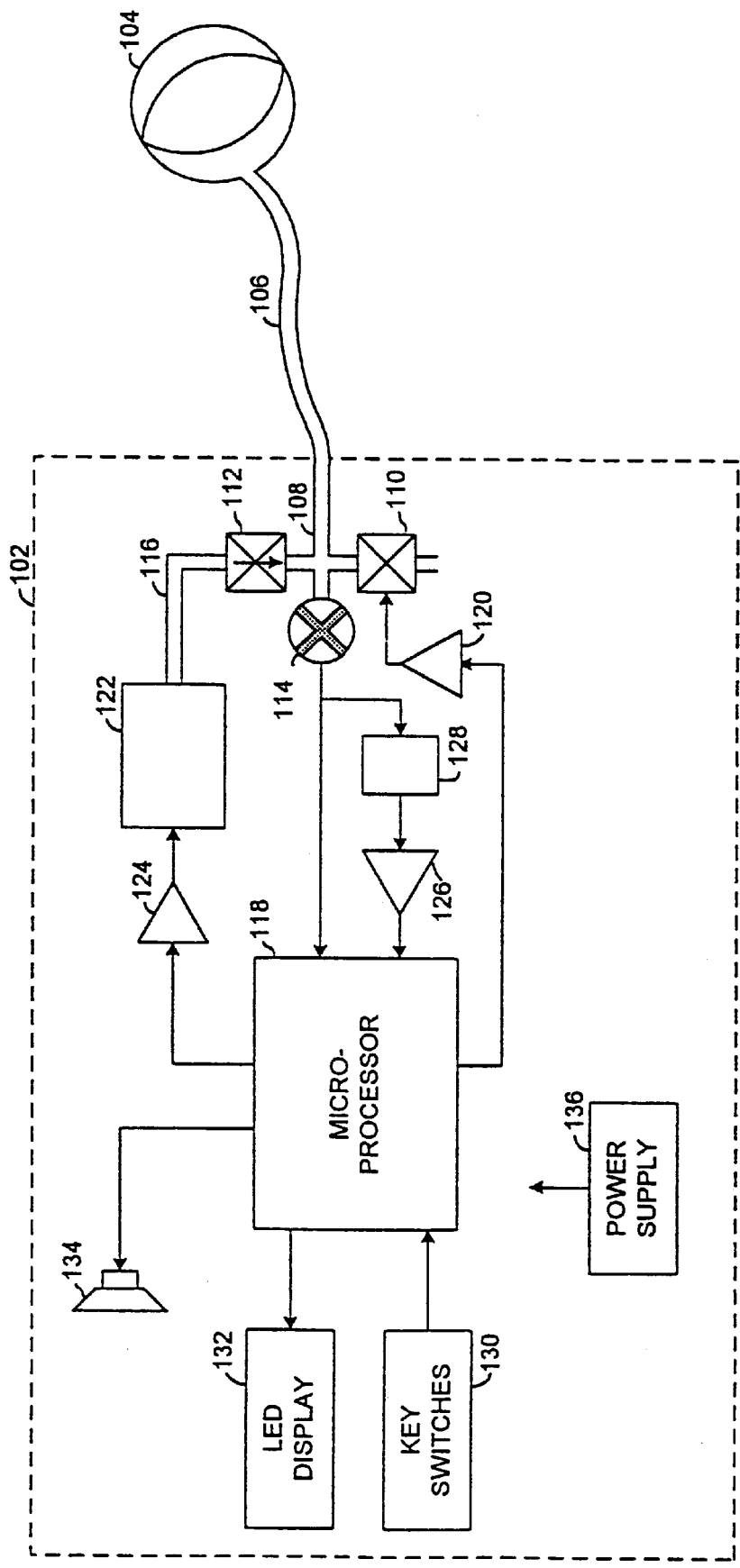
FIG. 1 is a block diagram of the preferred embodiment as employed in a pneumatic tourniquet system having one pneumatic tube connecting an inflatable tourniquet cuff to controlling instrumentation.

FIG. 1 depicts a pneumatic tourniquet system consisting of instrument 102 and pressurizing cuff 104 which can be inflated by instrument 102 to apply pressures to a patient limb. Instrument 102 is shown in block diagram form and is described below.

Cuff 104 is connected pneumatically by tubing 106 (15 feet of ⅛" ID flexible plastic tube) to manifold 108. Manifold 108 connects pneumatically tubing 106, valve 110 (EV0-3-6V Clippard Instrument Laboratory, Cincinnati OH), valve 112 and transducer 114 (MPX 5100 Motorola Semiconductor). Manifold 108 is constructed such that the physical distances between transducer 114 and valves 110 and 112 are minimized. Valve 112 is check valve which prevents the flow of gas from manifold 108 to tubing 116 when the pressure in manifold 108 is higher than the pressure in tubing 116.

Valve 110 in response to control signals generated by microprocessor 118 (80C196KB INTEL Corp., Santa Clara, Calif.), and conditioned by valve driver 120, pneumatically connects manifold 108 to atmosphere, allowing the release of pressure in cuff 104.

Pneumatic pump 122 is pneumatically connected to valve 112 by tubing 116. Pump 122 acts to pressurize cuff 104 in response to control signals generated by microprocessor 118 communicated through pump driver 124.

Pressure transducer 114 generates a cuff pressure signal which indicates the pressure-of gas in cuff 104, and the cuff pressure signal is then communicated to an analog to digital converter (ADC) input of microprocessor 118 which digitizes the cuff pressure signal. The cuff pressure signal is used by microprocessor 118 in combination with a cuff inflation signal, cuff deflation signal and a cuff pressure reference signal as described below, to regulate the pressure in cuff 104 near the reference pressure represented by the reference pressure signal by generating signals for the activation of pump 122 and valve 110.

The cuff pressure signal from pressure transducer 114 is also communicated to amplifier 126 through high pass filter 128. In this application of the invention high pass filter 128 is a simple RC filter with a bandpass of 50 Hz. The amplitude of the cuff pressure signal produced by pressure transducer 114 is approximately 5 mV per mmHg pressure applied. In the preferred embodiment amplifier 126 has a gain of 600 and a 3 dB bandwidth of 400 Hz. The resulting output of amplifier 126 is the AC component of the cuff pressure signal amplified and bandpass limited, this signal, hereinafter referred to as the reflected pressure pulse (RPP) signal is coupled to an analog to digital converter input of microprocessor 118. Microprocessor 118 analyzes the RPP signal to test for obstruction of tubing 106 as described below.

Key switches 130 connect to inputs of microprocessor 118, the user of instrument 102 may communicate with microprocessor 118 via key switches 130 to set a cuff reference pressure, set alarm limits and otherwise control instrument 102 as determined by the operating software of microprocessor 118.

Display 132 is connected to outputs of microprocessor 118, in the preferred embodiment display 132 consists of 7 segment LED's and appropriate interface electronics. In operation, microprocessor 118 may communicate to a user of instrument 102 the levels of various signals via display 132. These signals include but are not limited to the cuff pressure signal, cuff reference pressure signal and an obstruction alarm signal.

Audio transducer 134 is connected to an output of microprocessor 118 and is used by microprocessor 118 to alert the user of instrument 102 to alarm conditions.

In FIG. 1, power supply 136 provides regulated electrical power for the normal operation of all electronic and electrical components.

Microprocessor 118 regulates the pressure in cuff 104 near the reference pressure by controlling the activation of valve 110 and pump 122. At regular intervals of 30 ms microprocessor 118 enters a regulation subroutine. Within the regulation subroutine microprocessor 118 samples the cuff pressure signal, then computes a cuff pressure error signal from the difference of the cuff pressure signal and the cuff pressure reference signal, the cuff pressure error signal is then used in a proportional/integral control algorithm to calculate an activation time for either valve 110 or pump 122. New activation times for valve 110 and pump 122 are calculated each time the regulation subroutine is entered.

To ensure that the cuff pressure signal is representative of the actual pressure in cuff 104, microprocessor 118 periodically tests for obstruction of tubing 106.

At a rate determined by a obstruction test timer maintained by microprocessor 118, microprocessor 118 periodically checks for obstruction of tubing 106 by initiating an obstruction test subroutine, shown in FIG. 3. In the preferred embodiment an obstruction test is initiated once per second while the pressure in cuff 104 is being regulated. If tubing 106 has been found to be obstructed, the rate at which obstruction tests are initiated is increased to two per second. Once initiated an obstruction test proceeds as described below and shown in the flowchart depicted in FIG. 2. The activation of valve 110 and pump 122 by the regulation subroutine described above is suspended 202. The obstruction test subroutine next pauses for a period of 60 ms 204, this allows time for pressure in manifold 108, tubing 106 and cuff 104 to equalize and any pressure artifact produced by the operation of valve 110 and pump 122 to settle. Microprocessor 118 then initiates the sampling and storing of the RPP signal 206 at a rate of 1 sample per millisecond. The obstruction test subroutine continues by activating valve 110 for a period of 7 ms 208, due to the mechanical limitations of valve 110 this activation produces an actual valve opening time of approximately 3 ms.. The momentary activation of valve 110 introduces a pressure pulse of approximately 3 ms within the pneumatic system of instrument 102. The finite width of the pulse was determined by experimentation for this pneumatic system. Acquisition and storage of the RPP signal 210 then continues, in the preferred embodiment this sampling proceeds until 60 samples have been acquired. When acquisition of the RPP signal is complete 212 activation of valve 110 and pump 122 by the regulation subroutine is resumed 214.

Figure 2:
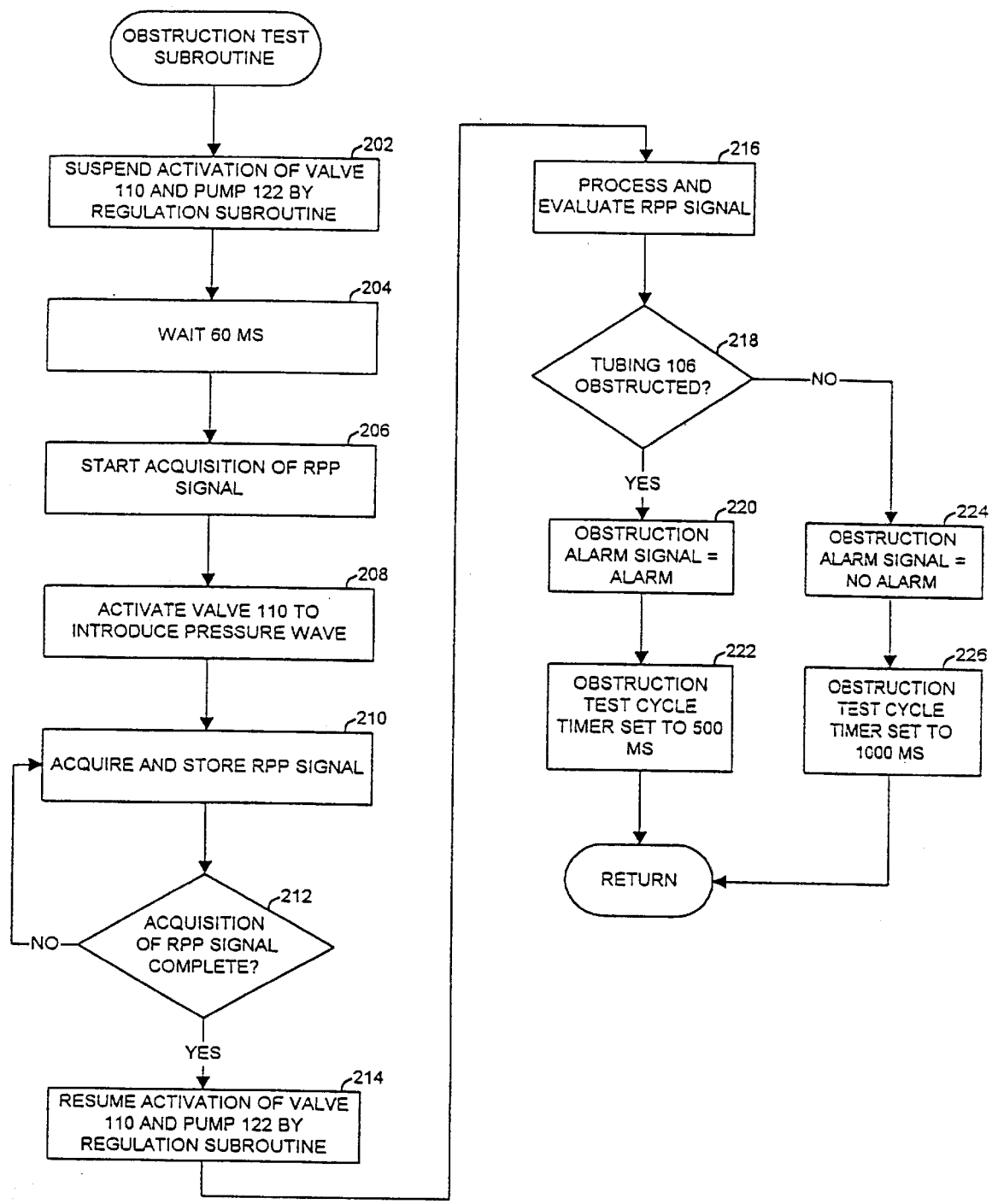
FIG. 2 is flow chart depicting the sequence of operations performed by the apparatus depicted in FIG. 1 when testing for obstruction.

The obstruction test subroutine shown in FIG. 2 continues by processing and evaluating the stored RPP signal 216 as described below. If evaluation of the RPP signal indicates that tubing 106 is obstructed 218, the level of an obstruction alarm signal maintained by microprocessor 118 is set to a level indicative of an obstruction alarm 220 and the rate of the obstruction test timer is adjusted to 500 ms 222. If evaluation of the RPP signal indicates that tubing 106 is not obstructed, the level of an obstruction alarm signal maintained by microprocessor 118 is set to a level indicative of the absence of an obstruction alarm 224 and the rate of the obstruction test timer is adjusted to 1000 ms 226.

When manifold 108 is pressurized the momentary opening of valve 110 and accompanying release of gas from manifold 108 produces a brief pressure variation within manifold 108 this pressure pulse then propagates along tubing 106 towards cuff 104 and is also sensed by transducer 114. The polarity of a pulse introduced by a momentary release of gas is defined to be negative. The amplitude of the introduced pressure pulse is primarily determined by the static pressure within the manifold 108, the opening time of valve 110 and the orifice size of valve 110. When the introduced pressure pulse encounters a change in the cross sectional area of tubing 106, a portion of the introduced pressure pulse is reflected back along tubing 106 towards transducer 114 and detected by transducer 114. The polarity and amplitude of this reflected pressure pulse in relation to the introduced pressure pulse are indicative of the degree of change in cross sectional area of tubing 106 at the region the reflection originated. The time elapsed between introduction of the pressure pulse and the detection of the reflected pressure pulse can be used to compute the round-trip distance to the region of tubing 106 where the cross sectional area change exists.

Figure 3A:
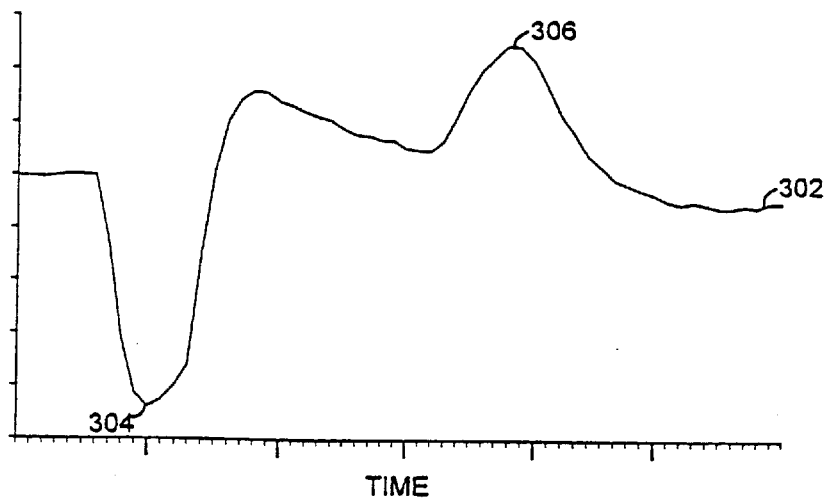
FIGS. 3a, 3b and 3c, are graphical representations of signals recorded from the apparatus shown in FIG. 1.

For example, at the point where tubing 106 enters cuff 104, which is equivalent to tubing 106 undergoing a substantial increase in diameter or cross sectional area, an introduced pressure pulse is reflected with a polarity change. FIG. 3a depicts the RPP signal recorded from the preferred embodiment when tubing 106 is not obstructed. In FIG. 3a the RPP signal is labeled as 302, the introduced pressure pulse is labeled as 304 and the reflected pressure pulse is labeled as 306. It can be seen in FIG. 3a that the reflected pressure pulse, is of the opposite polarity to the introduced pulse, and occurs 30 ms following the introduced pressure pulse. When the rate of propagation of a pressure pulse in the gas used to pressurize cuff 104 is known the distance from instrument 102 to cuff 104 can be calculated by multiplying the rate of propagation by the time elapsed between the introduction of a pressure pulse and the detection of the reflected pressure pulse and dividing this product by 2. In the case of the preferred embodiment the rate of propagation is approximately 1 foot per millisecond, the speed of sound in air, therefore, it can be calculated that cuff 104 is approximately 15 feet from instrument 102.

Figure 3B:
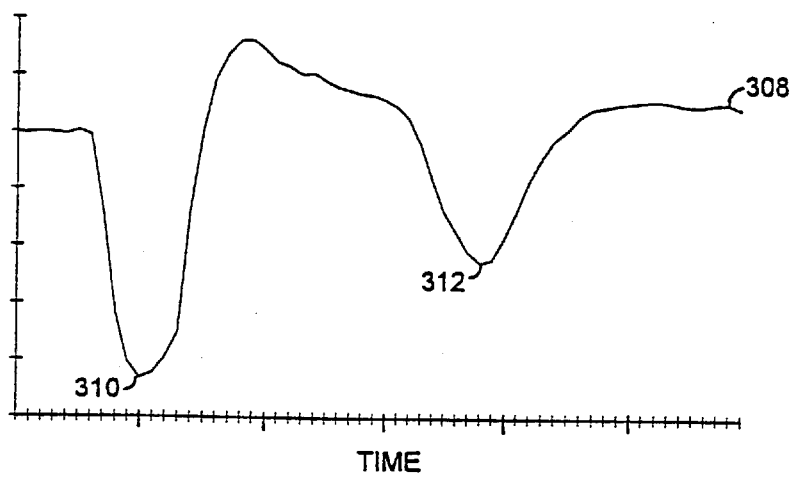

FIG. 3b depicts the RPP signal recorded from the preferred embodiment when tubing 106 is obstructed at the point where tubing 106 enters cuff 104. In FIG. 3b the RPP signal is labeled as 308, the introduced pressure pulse is labeled as 310 and the reflected pressure pulse is labeled as 312. It can be seen in FIG. 3b that the reflected pressure pulse is the same polarity as the introduced pulse, and occurs 30 ms following the introduced pressure pulse.

Figure 3C:
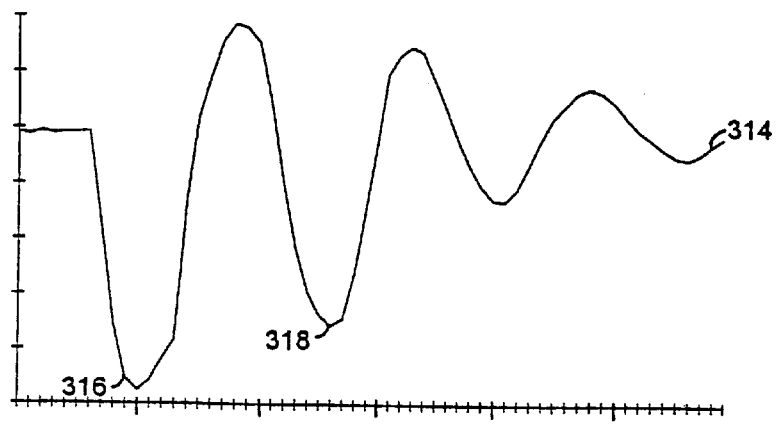

FIG. 3c depicts the RPP signal recorded from the preferred embodiment when tubing 106 is obstructed mid way between instrument 102 and cuff 104. In FIG. 3c the RPP signal is labeled as 314, the introduced pressure pulse is labeled as 316 and the reflected pressure pulse is labeled as 318. It can be seen in FIG. 3c that the reflected pressure pulse is the same polarity as the introduced pulse, and occurs 15 ms following the introduced pressure pulse. The other pulses which follow the reflected pulse 318 are reverberations of the introduced pressure pulse.

Within instrument 102 shown if FIG. 1, microprocessor 118, processes and evaluates the stored RPP signal to determine if tubing 106 has been obstructed by examining the amplitude of the reflected pressure pulse in relation to that of the introduced pressure pulse. If the polarity of the reflected pulse is the substantially the same as the introduced pulse and the amplitude of the reflected pulse exceeds a predetermined threshold established by experimentation, tubing 106 is determined to be obstructed, an obstruction alarm signal is set by microprocessor 118 to a predetermined level indicative of an obstruction alarm. If the polarity of the reflected pulse is substantially opposite to that of the introduced pressure pulse and exceeds a predetermined threshold also established by experimentation, the obstruction alarm signal is set to a predetermined level indicative of the absence of an obstruction alarm. During analysis of the stored RPP signal microprocessor 118 calculates the elapsed time between the introduced pressure pulse and the reflected pressure pulse and computes as described above the distance to the point along tubing 106 where the reflection originated. This distance may be displayed on display 132 to enable the user of instrument 102 to localize an obstruction.

When the obstruction alarm signal is set to a level indicative of an obstruction alarm, microprocessor 118 alerts the user of instrument 102 by enabling audio transducer 134 and displaying appropriate messages on display 132.

Those skilled in the art will recognize that the values of the various constants employed in the preferred embodiment such as the time valve 110 is opened to induce a pressure pulse in the pneumatic system, and the gain and bandwidth of amplifier 128 are particular to this particular implementation of the invention and that other constants may be chosen for other applications of the invention.

In the tourniquet system depicted in FIG. 1 and described above a pressure pulse is introduced in the pneumatic system by the rapid release of a small volume of gas from the pneumatic system, this method requires that the pneumatic system be pressurized to some level above atmospheric pressure. It will be obvious to those skilled in the art that a pressure pulse could be introduced in the pneumatic system by other means. For example, a pressure pulse could be introduced by the rapid addition of a small volume of gas through a valve connected to a gas source of higher pressure than the pneumatic system, or a pressure pulse could be introduced by rapidly varying the volume of a portion of the pneumatic system.

The pneumatic tourniquet system shown in FIG. 1 and described above has a single pneumatic connection to an inflatable cuff. Some pressurizing devices have more than one pneumatic connection to a single inflatable cuff, for example pneumatic tourniquet systems which have two pneumatic connections to a cuff, for improved regulation and safety. To better understand how the invention could be applied in such a device, an embodiment of the invention in a pneumatic tourniquet system having two pneumatic connections to a cuff is described below..

Figure 4:
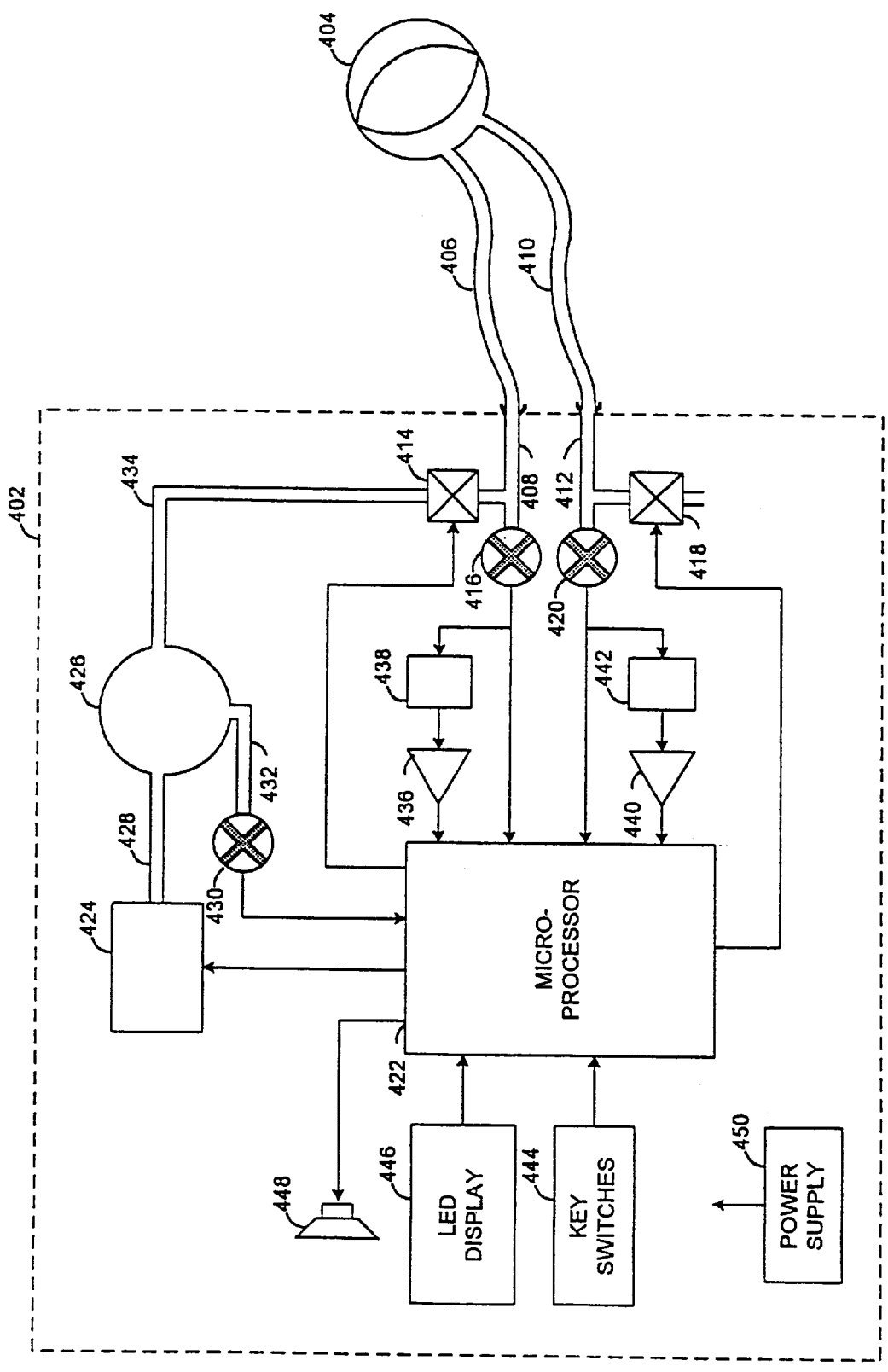
FIG. 4 is a block diagram of the preferred embodiment employed in a pneumatic tourniquet system having two pneumatic tubes connecting an inflatable tourniquet cuff to controlling instrumentation.

FIG. 4 depicts a pneumatic tourniquet system similar to the system shown in FIG. 1 and described above but having two pneumatic connections to a cuff. FIG. 4 shows a system consisting of instrument 402 and pressurizing cuff 404 which can be inflated by instrument 402 to apply pressures to a patient limb. Instrument 404 is shown in block diagram form and is described below.

Cuff 404 is connected pneumatically by tubing 406 to manifold 408 and by tubing 410 to manifold 412. Manifold 408 connects pneumatically tubing 406, valve 414 and transducer 416. Manifold 412 connects pneumatically tubing 408, valve 418 and transducer 420. Manifolds 408 and 412 are constructed such that the physical distances between the transducer and valve connections are minimized.

Valve 418 in response to control signals generated by microprocessor 422, pneumatically connects manifold 412 to atmosphere, allowing the release of pressure in cuff 404.

Pneumatic pump 424 is pneumatically connected to reservoir 426 by tubing 428. Pump 424 acts to pressurize reservoir 426 in response to control signals generated by microprocessor. Pressure transducer 430 which is pneumatically connected to reservoir 424 by tubing 430 generates a signal representative of the pressure in reservoir 424 which is communicated to an ADC input of microprocessor 422. Microprocessor 422 in response the reservoir pressure signal and a cuff pressure signal controls the activation of pump 424 to maintain in reservoir 426 a gas pressure 100 mmHg higher than that in cuff 404.

Tubing 434 pneumatically connects reservoir 426 to valve 414. Valve 414 in response to control signals generated by microprocessor 422, pneumatically connects manifold 408 to tubing 434 allowing the flow of gas from reservoir 426 and subsequent pressurizing of cuff 404.

Pressure transducers 416 and 420 generate cuff pressure signals which are indicative of the pressure of gas in cuff 404, and the cuff pressure signals are then communicated to ADC inputs of microprocessor 422 which digitizes the cuff pressure signals. The cuff pressure signals are used by microprocessor 422 in combination with a cuff inflation signal, cuff deflation signal and a cuff pressure reference signal as described below, to regulate the pressure in cuff 404 near the reference pressure represented by the reference pressure signal by generating signals for the activation of valve 414 and valve 418.

The cuff pressure signal from pressure transducer 416 is also communicated to amplifier 436 through high pass filter 438. The resulting output of amplifier 436, the reflected pressure pulse (RPP) signal for tubing 406, is coupled to an ADC input of microprocessor 422. Similarly, the cuff pressure signal from pressure transducer 420 is communicated to amplifier 440 through high pass filter 442. The resulting output of amplifier 440, the RPP signal for tubing 410, is coupled to an ADC input of microprocessor 422.

Key switches 444 connect to inputs of microprocessor 422, the user of instrument 402 may communicate with microprocessor 422 via key switches 444 to set a cuff reference pressure, set alarm limits and otherwise control instrument 402 as determined by the operating software of microprocessor 422.

Display 446 is connected to outputs of microprocessor 422. In operation, microprocessor 422 may communicate to a user of instrument 402 the levels of various signals via display 446. These signals include but are not limited to the cuff pressure signal, cuff reference pressure signal and an obstruction alarm signal.

Audio transducer 448 is connected to an output of microprocessor 422 and is used by microprocessor 422 to alert the user of instrument 402 to alarm conditions.

In FIG. 4, power supply 450 provides regulated electrical power for the normal operation of all electronic and electrical components.

Microprocessor 422 regulates the pressure in cuff 404 near the reference pressure by controlling the activation of valve 414 and valve 418. At regular intervals microprocessor 422 enters a regulation subroutine. Within the regulation subroutine microprocessor 422 samples the cuff pressure signals, then computes a cuff pressure error signal from the difference of the cuff pressure signals and the cuff pressure reference signal, the cuff pressure error signal is then used in a proportional/integral control algorithm to calculate an activation time for either valve 414 or valve 418. New activation times for valve 414 and valve 418 are calculated each time the regulation subroutine is entered.

To ensure that the cuff pressure signals are representative of the actual pressure in cuff 404, microprocessor 422 periodically tests for obstruction of tubing 406 and tubing 410. The obstruction test proceeds similarly to that described above for instrument 102 and shown in detail in FIG. 1. In instrument 402 the obstruction test proceeds as follows: the regulation of cuff 404 by the activation of valve 414 and valve 418 is suspended; after a predetermined interval pressure pulses are introduced into manifold 408 and manifold 412. A negative going pressure pulse is introduced into manifold 412 by the momentary activation of valve 418 and subsequent release of gas from manifold 412. This is identical to the method used to introduce pressure pulses in instrument 102 shown in FIG. 1 and described above. A positive going pressure pulse is introduced into manifold 408 by the momentary activation of valve 414 and subsequent release of gas into manifold 408 from reservoir 428. The resulting RPP signals from transducer 416 and transducer 420 are acquired and analyzed, the regulation of pressure in cuff 404 is then allowed to resume. As described above, the RPP signals are evaluated to test for obstruction of tubing 406 and 410 by comparing the polarity and amplitude of the introduced pressure pulse with that of the reflected pressure pulse. If the polarity of the reflected pressure pulse is the same as the introduced pressure pulse and the amplitude of the reflected pressure pulse exceeds a predetermined threshold the tubing is determined to be obstructed and an obstruction alarm signal set to a level indicative of an obstruction alarm.

Figure 5:
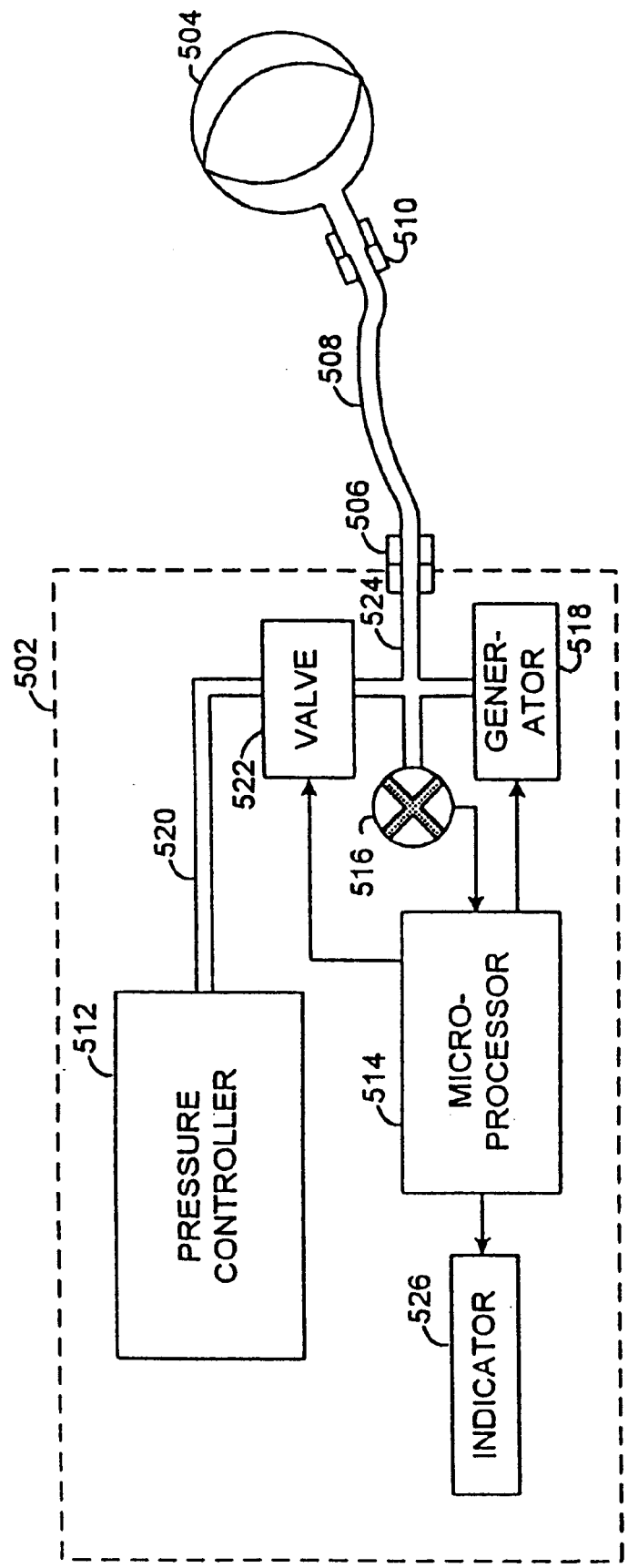
FIG. 5 is a more general block diagram of the preferred embodiment employed in pneumatic medical devices such as pneumatic tourniquet systems and pneumatic limb compression systems.

FIGS. 1 and 4 have shown the preferred embodiment incorporated into pneumatic tourniquet systems where components of the preferred embodiment have been used to both regulate and control pressures as well as characterize the pneumatic system. A more general representation of the preferred embodiment is shown in FIG. 5. This is a more general representation of FIG. 1 and FIG. 4 and is included to illustrate how the invention might be applied to other pneumatic medical devices which comprise a pressure controller connected by pneumatic tubing to an inflatable cuff or appliance having a diagnostic or therapeutic function.

Shown in FIG. 5 is a pneumatic limb compression system consisting of instrument 502 connected to a pressurizing sleeve 504 via pneumatic connector 506, tubing 508 and pneumatic connector 510. Pressure controller 512 supplies gas for the pressurization of sleeve 504 and controls the pressure of gas in sleeve 504.

Microprocessor 514, pressure transducer 516 and pressure pulse generator 518 comprise a pneumatic reflectometer for monitoring the patency of the pneumatic connection between instrument 502 and sleeve 504. If sleeve 504 becomes disconnected from instrument 502 at pneumatic connector 508 or 510 a change in length of the pneumatic connection will be detected. If tubing 508 becomes obstructed this to will be detected.

Tubing 520 pneumatically connects pressure controller 512 to valve 522. Valve 522 is a normally open valve which pneumatically connects tubing 520 to manifold 524, when activated valve 522 closes and pneumatically isolates pressure controller 512 from the rest of the pneumatic system. Manifold 524 pneumatically connects valve 522, pneumatic connector 506, transducer 516 and pressure pulse generator 518, Manifold 524 is constructed such that physical distance between transducer 516 and pressure pulse generator 518 is minimized.

Microprocessor 514 controls the activation of valve 522 and pressure pulse generator 518, and process and evaluates signals arising from transducer 516. The signal from transducer 516 which is representative of changes in the pressure in the pneumatic system is coupled to an analog to digital (ADC) input of microprocessor 514.

In operation microprocessor 514 periodically tests for the obstruction of tubing 508 as follows: microprocessor 514, first activates valve 522 to isolate the pneumatic system of pressure controller 512 from manifold 524. After a period of time sufficient in duration to allow any pneumatic artifact caused by the closure of valve 522 to dissipate, microprocessor 514 next begins to acquire and evaluate the signal arising from transducer 516 and activates pressure pulse generator 518. Pressure pulse generator 518 introduces into manifold 524 a pressure pulse which propagates along tubing 508 towards sleeve 504. The pressure pulse introduced by generator 518 is of sufficient amplitude and duration as to enable transducer 516 to detect reflected pressure pulses which are produced by the introduced pressure pulse encountering regions in tubing 508 where the diameter or cross sectional area under go change. For example, reflections of the introduced pressure pulse are produced from where tubing 508 enters sleeve 504 and where tubing 508 may be obstructed.

Microprocessor 514 processes and evaluates the signals arising from transducer 516 as described above by comparing the amplitude of the introduced pressure pulse with that of any detected reflected pressure pulses. If the polarity of the reflected pulse is the same as the introduced pressure pulse and the amplitude of the reflected pressure pulse exceeds a predetermined threshold tubing 508 is determined to be obstructed and indicator 526 is activated. When the rate of propagation of a pressure pulse in the gas used to pressurize sleeve 504 is known, microprocessor 514 can calculate the distance from instrument 502 to the point along tubing 508 from which the reflection arose. This distance may be displayed by microprocessor 514 on indicator 526 to assist a user of instrument 502 in locating an obstruction and taking corrective action.

We claim:

1. A method of monitoring the patency of pneumatic tubing, comprising the steps of:
   generating a pneumatic pulse at one part of pneumatic tubing by varying the pressure in the tubing during a finite time interval;

sensing at a second part of the tubing a variation of the pressure at the second part after the finite time period; and producing a human-perceptible signal when the sensed pressure variation exceeds a reference level.

2. The method of claim 1 wherein the generating step comprises the step of rapidly varying the volume of a portion of the tubing, thereby to generate the pneumatic pulse.

3. A method of monitoring the patency of pneumatic tubing, comprising the steps of:

generating a pneumatic pulse within the pneumatic tubing by varying the pressure in the tubing during a finite time interval;

sensing the variation of the pressure in the tubing after the finite time period; and producing a human-perceptible signal when the sensed pressure variation exceeds a reference level.

4. The method of claim 3 wherein the generating step comprises the step of rapidly varying the volume of a portion of the tubing, thereby to generate the pneumatic pulse.

5. A method of monitoring the patency of pneumatic tubing used with a medical device, comprising the steps of:

generating within the tubing a propagating pneumatic pulse having an amplitude;

sensing the amplitude of the pulse during a first time period;

sensing the amplitude of the pulse during a second time period that is subsequent to the first time period;

calculating a pressure variation corresponding to the difference between the pulse amplitude as sensed during the first and second time periods; and producing a human-perceptible signal when the pressure variation exceeds a predetermined reference level.

6. The method of claim 5 wherein the generating step comprises the step of rapidly varying the volume of a portion of the tubing, thereby to generate the pneumatic pulse.

* * * * *